United States Patent [19]

Miyazaki et al.

[11] Patent Number: 5,370,842
[45] Date of Patent: Dec. 6, 1994

[54] SAMPLE MEASURING DEVICE AND SAMPLE MEASURING SYSTEM

[75] Inventors: Takeshi Miyazaki, Ebina; Matsuomi Nishimura, Ohmiya; Takayuki Yagi, Machida; Kazumi Tanaka, Yokohama; Toshikazu Ohnishi, Machida; Masanori Sakuranaga, Atsugi; Yoshito Yoneyama, Kawasaki; Hidehito Takayama, Chigasaki; Kazuo Isaka, Tokyo, all of Japan

[73] Assignee: Canon Kabushiki Kaisha, Tokyo, Japan

[21] Appl. No.: 979,811

[22] Filed: Nov. 20, 1992

[30] Foreign Application Priority Data

Nov. 29, 1991 [JP] Japan .................................. 3-316481
Oct. 2, 1992 [JP] Japan .................................. 4-264895

[51] Int. Cl.⁵ .................. G01N 21/00; G01N 21/85; B01L 21/85
[52] U.S. Cl. .................. 422/82.06; 422/82.04; 422/82.05; 422/100; 356/410
[58] Field of Search .............. 422/82.06, 82.05, 82.04, 422/81, 100, 103; 356/410, 411, 414, 440; 250/576, 575; 417/213, 228

[56] References Cited

U.S. PATENT DOCUMENTS

| 3,661,460 | 6/1972 | Elking et al. | 356/36 |
|---|---|---|---|
| 3,705,771 | 12/1972 | Friedman et al. | 356/39 |
| 3,992,109 | 11/1976 | Bock | 250/573 |
| 4,099,882 | 7/1978 | Andrén et al. | 356/411 |
| 4,398,894 | 8/1983 | Yamamoto | 422/82 |
| 4,436,827 | 3/1984 | Tamagawa | 356/440 |
| 4,566,791 | 1/1986 | Goldsmith | 356/410 |
| 4,637,729 | 1/1987 | Schoch | 356/410 |
| 4,723,129 | 2/1988 | Endo et al. | 346/1.1 |
| 4,740,796 | 4/1988 | Endo et al. | 346/1.1 |
| 4,794,806 | 1/1989 | Nicoli et al. | 250/576 |
| 4,863,264 | 9/1989 | Miyake et al. | 356/39 |
| 4,867,559 | 9/1989 | Bach | 356/440 |
| 4,999,582 | 3/1992 | Parks et al. | 422/82.02 |
| 5,052,897 | 10/1991 | Yamashita et al. | 417/228 |
| 5,125,747 | 6/1992 | Sayegh et al. | 356/410 |
| 5,171,132 | 12/1992 | Miyazaki et al. | 417/413 |
| 5,183,740 | 2/1993 | Ligler et al. | 422/82.05 |

FOREIGN PATENT DOCUMENTS

| 347579 | 12/1989 | European Pat. Off. | B01L 3/00 |
|---|---|---|---|
| 63-70165 | 3/1988 | Japan | G01N 33/483 |
| 8100911 | 4/1981 | WIPO | 356/410 |

Primary Examiner—Robert J. Warden
Assistant Examiner—Christopher Y. Kim
Attorney, Agent, or Firm—Fitzpatrick, Cella, Harper & Scinto

[57] ABSTRACT

An injection port for injecting a sample, an accumulation portion for accumulating the injected sample having a reagent carrier enclosed, a flow passage portion, having a light receiving element at a measuring position located halfway thereof, for passing a reaction fluid having reacted with the reagent in the accumulation portion therethrough, a micro-pump having a feed action of the sample fluid within the flow passage portion and which is a heat generating element provided near a nozzle downstream of the measuring position of the flow passage portion are formed integrally and intensively as a cartridge by a producing method including a semiconductor fabrication process.

17 Claims, 21 Drawing Sheets

FIG. 17A
FIG. 17B
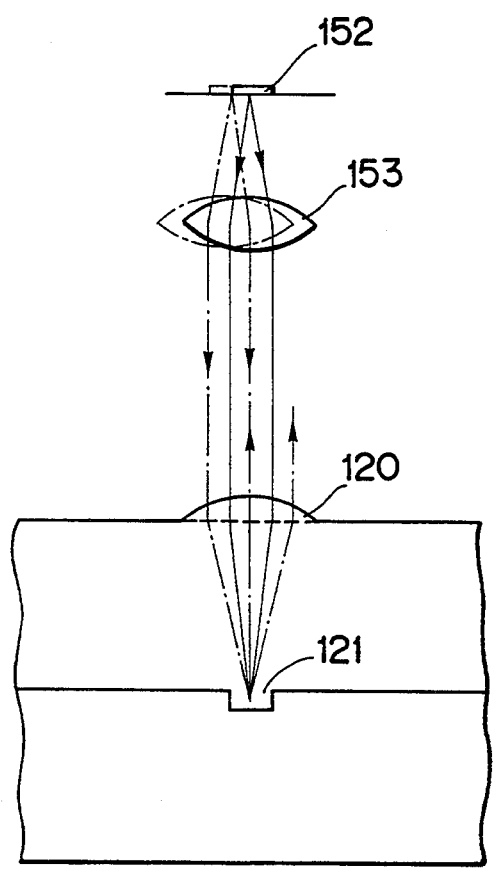
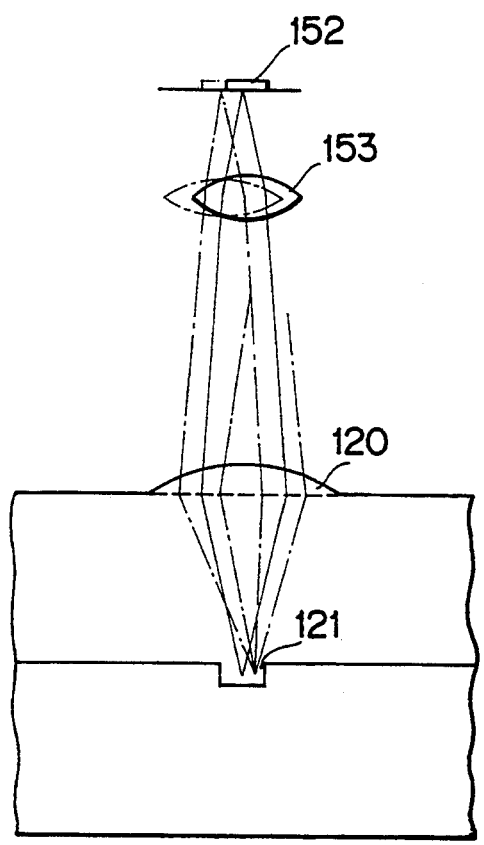

SAMPLE MEASURING DEVICE AND SAMPLE MEASURING SYSTEM

BACKGROUND OF THE INVENTION

1. Field of the Invention

The present invention relates to a technical field for measuring components in a sample by using antigen-antibody reaction or hybridization of nucleic acid, or for measuring fine objects such as cells, micro-organisms or chromosomes.

2. Related Background Art

Recent advancements in the technology for detection of minor components have played a great role for early diagnosis of various diseases or prognostic diagnosis in the field of clinical examinations. Since 1958, when a method of determining insulin with labeling of radioactive iodine was publicized by S. A. Berson, it has been possible to measure plasma protein such as IgE, IgG, CRP or micro-globulin, tumor marker such as AFP, CEA or CA19-9, hormones such as TSH or $T_3$, blood drugs, virus such as HBV or HIV and its sample, nucleic acid such as DNA or RNA, and it has been possible to perform many sample processings by automatization.

For most of these biological minor components, an immunological method using antigen-antibody reaction or a method using nucleic acid—nucleic acid hybridization has been employed. Example of such analytical methods is that the antigen-antibody reaction or nucleic acid hybridization with the sample is carried out by fixing antigen, antibody or single chain nucleic acid bonding specifically with the sample as a probe onto solid phase surfaces such as particles, beads or walls in an accumulation portion. Antigen-antibody compound or double chain nucleic acid is detected to determine the sample, using a labeled substance having specific interaction carrying a labeling substance with high detection sensitivity such as enzyme, fluorescent material or luminescent material, for example, labeled antigen, labeled antibody or labeled nucleic acid.

FIG. 20 is a view showing an example of a conventional apparatus for making the above-mentioned measurement. An insoluble carrier 202 having a reagent fixed on the surface thereof is contained in a reaction bath 201, to accumulate a sample fluid therein, causing the reaction and making a reaction fluid 203. The reaction fluid 203 is passed through a fluid feed pipe 204 and a valve 205 to be once stored in a syringe-type pump 206. Next, the valve 205 is switched to feed the stored reaction fluid to an optical cell 207 which is in a measurement location. The optical cell 207 is illuminated from a light source 208, and the light passing through the reaction fluid is detected by a light receiving element 209, whereby the colorimetry for the coloration reaction or fluorometry in the reaction fluid is carried out. The reaction fluid after the measurement is discharged as a waste fluid.

On the other hand, an apparatus in which a number of fine particles such as cell particles or chromosomes contained in a particle suspended fluid such as a blood sample are separated one by one to flow away and individual particle is measured with an optical or electrical method, has been put to practical use as a flow cytometer or particle counter.

FIG. 21 is a view showing an example of a conventional flow cytometer. A sample fluid which is a particle suspended fluid, is contained in a test tube 220, while a sheath fluid composed of PH buffer and physiological salt fluid is contained in a sheath bottle 223. Each fluid is once stored in a syringe-type pump 222, 225, and each valve 221, 224 is switched to feed the fluid by applying a pressure to the stored fluid. The sample fluid is supplied to a sample nozzle 226, and the sheath fluid is supplied to the surroundings 227 around the sample nozzle 226. Owing to a sheath flow principle, the sample fluid is converged hydrodynamically while being surrounded by the sheath fluid, and particles in the sample fluid are separated one by one to flow through a flow portion 228. Light is directed to the flow of particles from a light source 229 to measure the fluorescent or scattered light emitted from particles illuminated by light receiving elements 230, 231. A number of particles are sequentially measured, and the analysis for the kind or property of particles is made using a statistical method on the basis of the output from the elements. It is necessary to flush a fluid feed passages with a cleaning fluid every time one sample is measured, and a cleaning mechanism (not shown) is provided therefor.

SUMMARY OF THE INVENTION

The conventional apparatus as above described, however, inevitably contains a dead space of the flow passage owing to long fluid feed passages or a pressure pump, thus necessitates useless sample fluid. Along with the use of a large quantity of sample fluid, the amount of waste fluid will increase undesirably in the respect of environmental problems such as biohazard.

Also, in the conventional apparatus as above described, the sample fluid is supplied to a measuring unit by applying a pressure to each fluid, for this reason a pressure mechanism such as piping and pump is needed, so that the apparatus becomes large and complex to control. Also, there is a limitation in reducing the size of apparatus. Furthermore, there is a certain time lag for forming a flow in the measuring unit or stopping the flow, so that the control response is poor.

In light of the above-mentioned problems, the present invention has the following objects:

(1) To provide a smaller-sized and intensified measuring device that requires a smaller amount of sample by making the dead space of the flow passage for a liquid sample as small as possible.

(2) To provide a measuring device capable of performing the measurement without damaging the sample and coping with environmental problems such as biohazard countermeasure.

(3) To provide a measuring device having a stable performance at a lower cost.

Further objects of the present invention will be apparent from the following description of the embodiments.

BRIEF DESCRIPTION OF THE DRAWINGS

FIGS. 17A and 17B are views for explaining the features of the system as shown in FIG. 16.

DETAILED DESCRIPTION OF THE PREFERRED EMBODIMENTS

Figure 1:
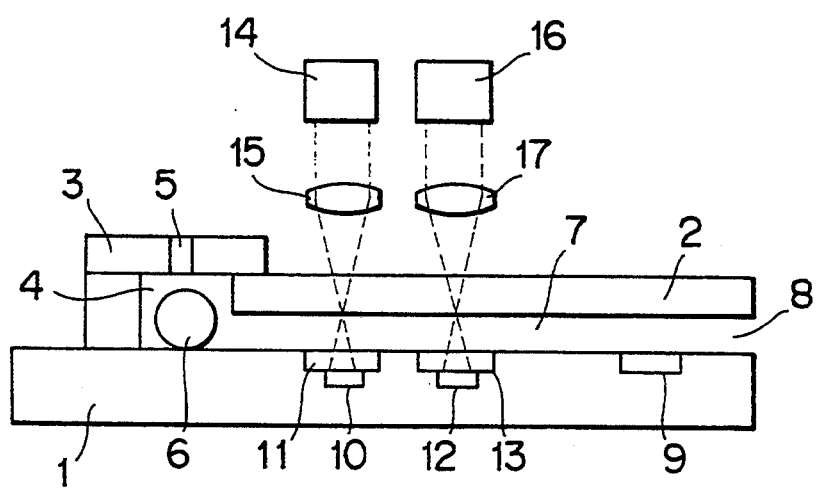
FIG. 1 is a side view showing a constitution of a cartridge according to an embodiment.
Figure 2:
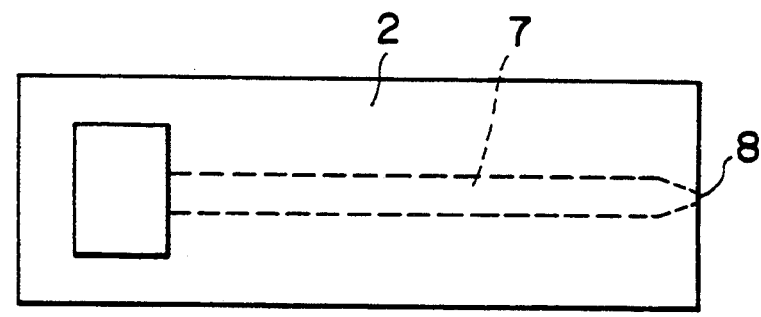
FIG. 2 is a top view of a second substrate and a first substrate constituting the cartridge, respectively.
Figure 2:
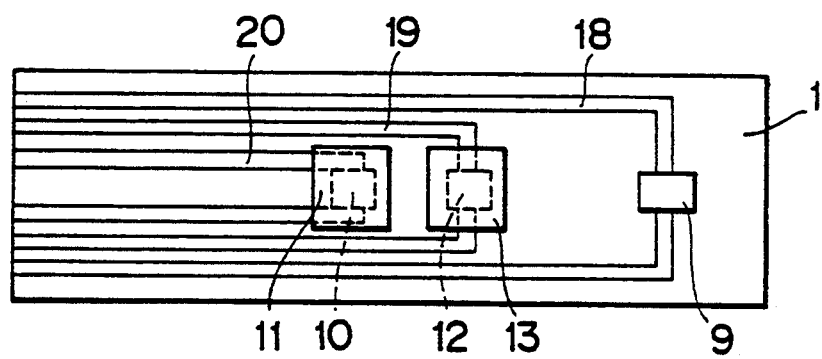
Figure 3:
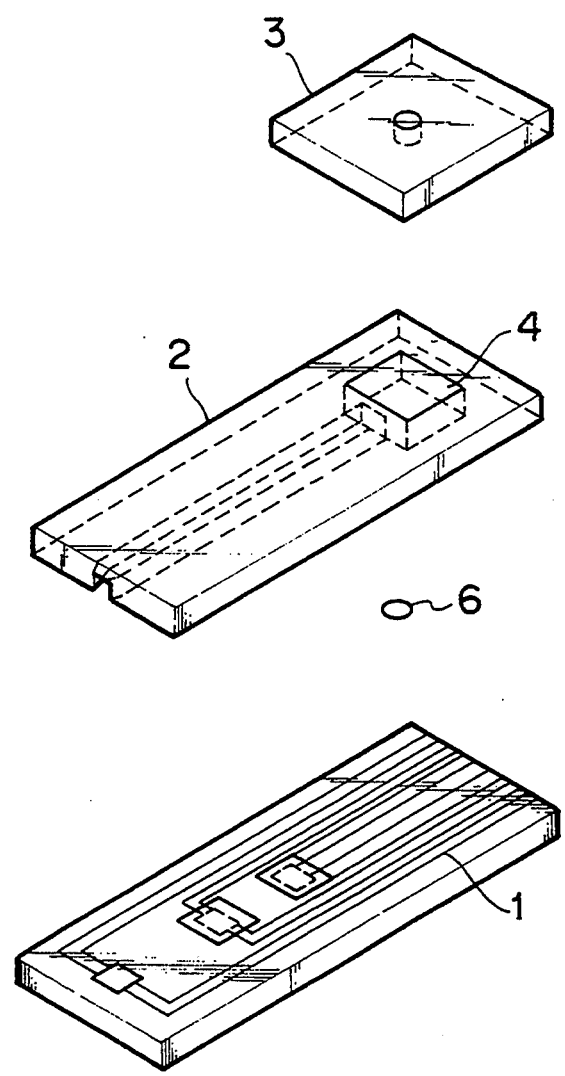
FIG. 3 is an assembling view of the cartridge.

A cartridge, according to a first embodiment of the present invention, will be described below in which a sample is reacted with a reagent to obtain a reaction fluid, by repeating the cleaning and reaction as necessary, and the reaction fluid is optically measured for measurement of the sample. FIG. 1 is a side view showing a structure of the cartridge according to the first embodiment, FIG. 2 is a top view from above of a first substrate and a second substrate, and FIG. 3 is an assembling view of the cartridge.

The cartridge of this embodiment has a constitution in which the first substrate 1, the second substrate 2 and a third substrate 3 are bonded, wherein the first substrate 1 is a silicone substrate, and the second substrate 2 and the third substrate 3 are glass substrates. A space for an accumulation portion 4 that is a reaction bath is formed within the cartridge by the bonding of the substrates. The third substrate 3 is provided with an injection port 5 which is a hole for injecting the liquid such as a sample fluid, thus it is possible to inject the sample fluid from the outside into the accumulation portion 4. A spherical insoluble carrier 6 having a reagent fixed on the surface thereof is enclosed within the accumulation portion 4. The insoluble carrier 6 is composed of a ceramic such as glass, a plastic made of high molecular compounds, a metal such as magnetic substance, or a composite material thereof, and has been subjected to surface treatment with covalent bond group introduced so as to facilitate the fixing of reagent. The insoluble carrier 6 is not limited to a spherical shape, but may take other shapes such as polyhedron, and exist in plural number but not one. Alternatively, the reagent may be directly fixed to an inner wall of the accumulation portion 4 without the use of the insoluble carrier. The reagent will be described in detail later.

The accumulation portion 4 is connected with a flow passage portion 7, which has a nozzle opening 8 as outlet port in an end portion thereof. The nozzle opening 8 has a tapered shape so as to have a line resistance action. A micro-pump 9 is formed near the nozzle opening 8, on the first substrate 1. The micro-pump 9 specifically has a structure in which a heat generating element is attached to the flow passage portion 7 by a manufacturing method as will be described later. When a pulse voltage is applied to the heat generating element, a sample fluid heated by heat generating will instantaneously evaporate, thereby producing a bubble, and the sample fluid is discharged as a droplet through the nozzle opening due to a pressure caused by impact of the bubble expanding or shrinking, so that a minute amount of the sample fluid is delivered through the flow passage portion. And the sample fluid in relation to an amount of the discharged fluid is drawn from the accumulation portion 4 in a direction toward the nozzle opening in the flow passage portion and supplied thereto. By repeating the discharge at high frequencies continuously the liquid feeding action of the sample fluid can be obtained, thus it is possible to form a fluid flow within the flow passage portion 7.

Figure 7A:
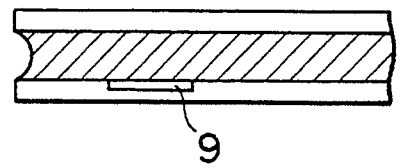
FIGS. 7A to 7E are views for explaining the action of a micro-pump.
Figure 7B:
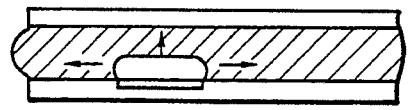
Figure 7C:
Figure 7D:
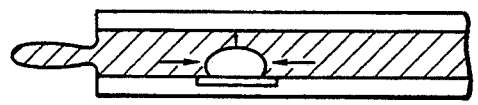
Figure 7E:
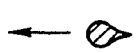
Figure 7E:
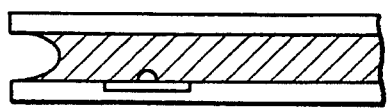

FIGS. 7A to 7E are views for specifically explaining how a bubble is generated and a liquid droplet is discharged. In an initial state as shown in FIG. 7A, when a pulse voltage is instantaneously applied to the heat generating element and then the element is heated, the water content near the heat generating element evaporates, and a bubble is generated as shown in FIG. 7B. Thus, the volume thereof expands in relation to an amount of the evaporation, so that the liquid near the nozzle opening is extruded out of the nozzle opening as shown in FIG. 7C. The bubble initially expanding is cooled and starts to shrink as shown in FIG. 7D, so that the liquid discharged through the opening due to contraction of the volume becomes a liquid droplet to fly in the air as shown in FIG. 7E. The liquid is supplied by an amount of the discharged fluid due to capillary phenomenon, and returns to the initial state of FIG. 7A. The basic principle of discharging liquid droplets with bubbles has been described in U.S. Pat. No. 4,723,129 and No. 4,740,796.

The micro-pump may take another form in which a piezoelectric element is used instead of the heat generating element, whereby a pulsed voltage is applied to the piezoelectric element, and a liquid droplet is discharged due to a pressure caused by impact of change in volume of the piezoelectric element.

On the surface of the first substrate 1, there are provided the above-mentioned micro-pump and a sensitive element for measuring the sample fluid. Specifically, in order to optically detect the state of sample fluid, a first photodetector element 10, a first optical filter 11 having wavelength selection characteristic, a second photodetector element and a second optical filter 13 are formed on the substrate by a manufacturing method as will be described later. These members constitute an optical detecting portion for selectively receiving first and second lights arriving via the sample fluid. While this embodiment is directed to an example of optically measuring the sample fluid, it should be noted that the sample fluid may be measured by an electrical or magnetic method, for example. Furthermore, it may be measured in a composite form thereof. In this case, like the optical detecting portion of FIG. 1, it is necessary that a sensitive element (e.g., electrode, magnetic detector element) suitable for respective measurement be bonded on the substrate.

As shown in FIG. 2, a heat generating element of micro-pump 9 and first and second photodetector elements 10, 12 for the micro-pump are bonded on the first substrate 1. Those elements are connected with electrical conductive patterns 18, 19, 20, which are patterned on the surface of the first substrate 1, as illustrated. When the first substrate 1 and the second substrate 2 are bonded, end portions of the conductive patterns 18, 19, 20 are exposed to the exterior so as to contact and electrically conduct with external terminals.

The above members are integrally assembled to make up a cartridge. The manufacturing method of cartridge will be described later. On the other hand, in order to examine the degree of coloration for the sample fluid or generate the fluorescent or scattered light from the sample fluid by directing the illuminating light that is a measurement energy to the sample fluid within the flow passage portion 7, a light illuminating portion composed of light sources 14, 16 and condenser lenses 15, 17 is provided apart from the cartridge, as shown in FIG. 1. The light sources 14, 16 are exemplified suitably by a semiconductor laser, LED, a halogen lamp, a tungsten lamp, or a mercury lamp. In the case that the light emitting from a sample itself such as chemiluminescence or bioluminescence is detected for the measurement, there is no need for light illumination and thus the provision of any light illuminating portion.

In this embodiment, a micro-pump provided near the outlet port downstream of a measurement position can offer a great superiority peculiar to the sample measurement as described in the following.

If the micro-pump is provided at upstream of the measurement position, there is a fear that a pressure variation or heat produced by the pump action has an adverse effect such as degeneration or damage on the sample fluid or cell particles near the pump and it is measured. On the contrary, the micro-pump is provided on the downstream side, whereby adverse effect on the sample before measurement can be prevented. In addition, a waste liquid after measurement is subjected to pressure or heat on the downstream position, therefore, the disinfection or sterilization action for the waste liquid can be obtained so as to meet a biohazard countermeasure.

Also, since a micro-pump is provided near the outlet port to draw the liquid in relation to the amount of discharge through the nozzle and to create a flow in the flow passage portion, a stable fluid system can be obtained with a high control responsiveness for the control of fluid. Further, there is less dead space for the fluid system, so that the use amount of sample is only a little.

Figure 4:
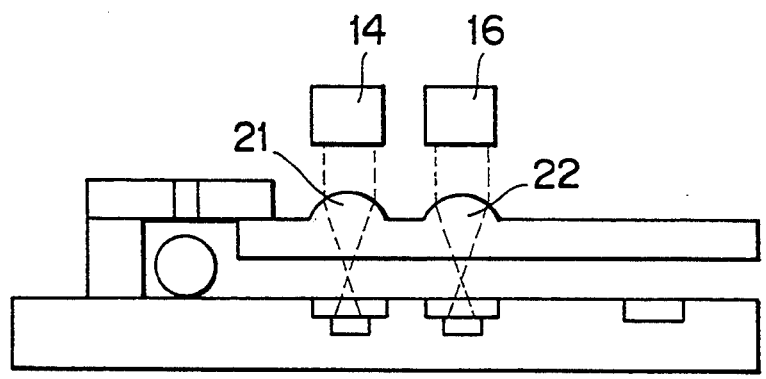
FIG. 4 is a view showing a first variation of the embodiment.
Figure 5:
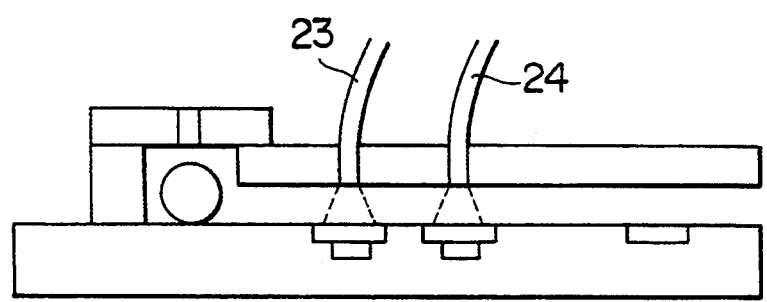
FIG. 5 is a view showing a second variation of the embodiment.
Figure 6:
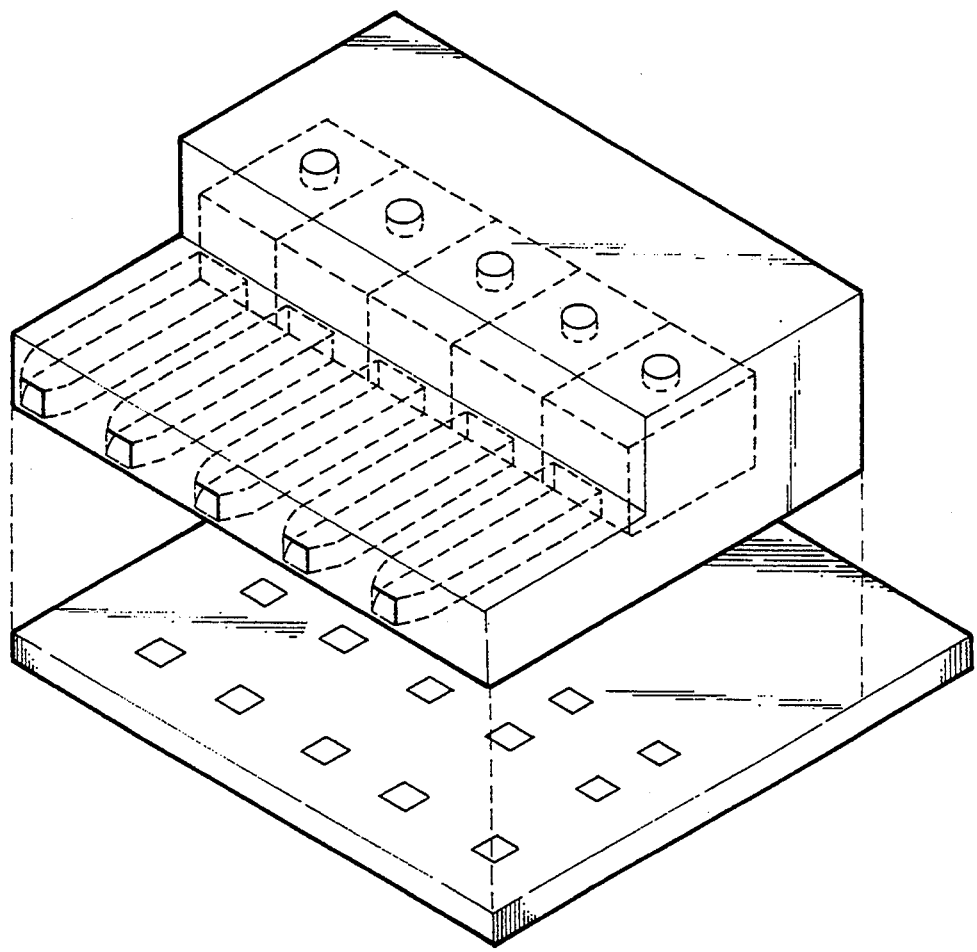
FIG. 6 is a view showing a third variation of the embodiment.

Several variations of the above-described cartridge will be described below. FIG. 4 shows an example in which condenser lenses 21, 22 are integrally formed on an upper face of the substrate. The condenser lens is exemplified by a spherical lens, a Fresnel lens, or a zone plate. FIG. 5 shows an example in which the illuminating light is introduced using optical fibers 23, 24, and has advantage that there is no need of making an optical axis alignment between the light source and the cartridge. FIG. 6 illustrates further development from the above-described example, and shows an example of cartridge in which measuring modules each consisting of an accumulation portion, a flow passage portion and elements are arranged in parallel on one sheet of the substrate at a high density to make an array thereof.

Next, the manufacturing method of the cartridge will be described in detail. Since the cartridge of the embodiment can be readily produced by the micro-mechanics technique including a semiconductor producing process, it is suitable for the mass production with batch processing. Also, the array formation as shown in FIG. 6 is easily made. The manufacturing process is mainly composed of the following four processes.

Process 1

A bore serving as the accumulation portion 4 is provided on a glass substrate which is the second substrate 2, further a groove serving as the flow passage portion 7 is formed. The method of forming the groove on the glass substrate is to remove the substrate partially by sensitizing a light sensitive glass by photolithography, or by etching the glass to a desired depth with hydrofluoric acid. Another method is to apply a resist on a glass substrate or a silicone substrate, for example, and make a development by photolithographic process to be then solidified, thus a resist removal portion may be used as the groove. Also, the groove can be formed by anodic bonding a silicone substrate having the patterns of the accumulation portion and the flow passage portion formed by etching, onto a glass substrate.

While the glass substrate is processed to form the groove in this embodiment, it will be appreciated that the groove may be formed on the second substrate by molding with the mold producing method using a transparent resin material.

Process 2

Figure 8:
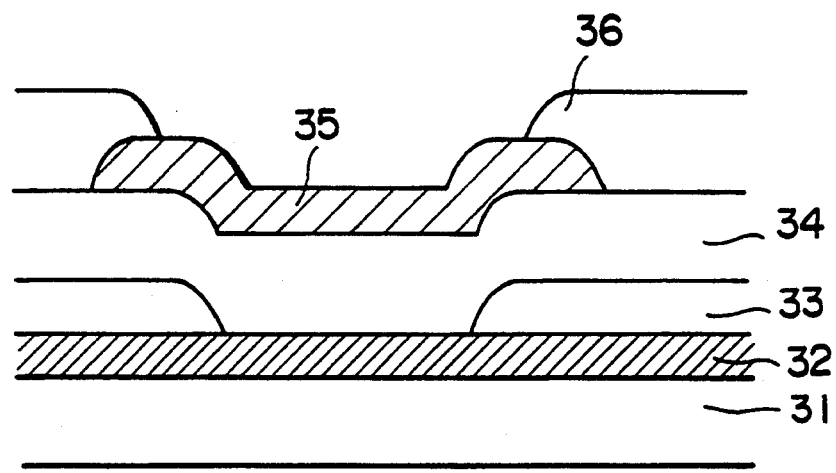
FIG. 8 is a view showing a structure of a heat generating element for the micro-pump.

A heat generating element of the micro-pump is bonded onto a silicone substrate which is the first substrate 1. FIG. 8 shows a detailed constitution of the heat generating element for the micro-pump which is formed on the silicone substrate. This manufacturing process is as follows: After a silicone oxide film is formed on a silicone substrate 31, $HfB_2$ layer 32 and Al layer 33 are laminated, and formed as a heat generating portion and an electrode portion, respectively, using photolithographic process. Further, $SiO_2$ as an insulating layer 34 and Ta as a protective layer 35 are sequentially laminated on a portion excluding a wire bonding portion of the electrode portion. Thereafter, only Ta is patterned like a stripe on the periphery around the heat generating portion by the photolithographic process. And a resin layer 36 is patterned on the $SiO_2$ layer not covered by Ta so as to isolate the electrode away from the sample liquid, thus the heat generating element serving as a pump portion is produced.

Process 3

Figure 9:
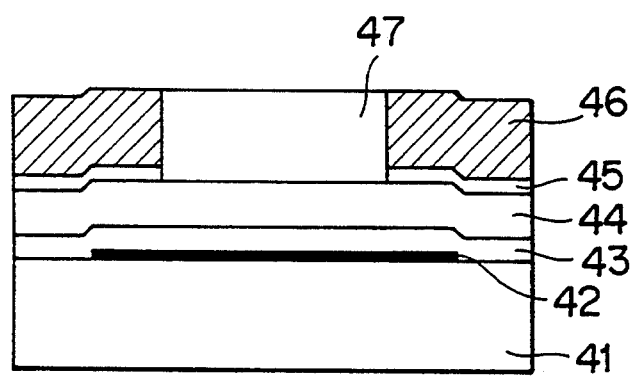
FIG. 9 is a view showing a structure of an optical detecting portion.

Two optical detecting portions are bonded onto the silicone substrate serving as the first substrate 1. FIG. 9 shows a detailed constitution of the optical detecting portion formed on the silicone substrate. The manufacturing process of this optical detecting portion is as follows: Cr film 42 is formed 0.1 μm thick on a glass substrate 41 by resistance heating. The substrate is heated to 350° C., and SiN:H layer 43 is formed 0.3 μm thick in a mixed gas of $SiH_4$ and $NH_4$ (10 CCM:20 CCM) by plasma CCD. In the same vacuum, the susbtrate is heated to 200° C., and α-Si:H layer 44 is formed 0.6 μm thick in an $SiH_4$ gas by plasma CVD. By adding $PH_3$ gas to $SiH_4$ gas, $n^+$-α-Si:H layer 45 is formed in a thickness of 0.2 μm. Al layer is formed in a thickness of 0.1 μm by electron beam vapor deposition. The Al layer is patterned in the photolithographic process to form an electrode 46. An opening portion is provided in the n+-α-Si:H layer 45 in $CF_4$ gas by RIE (reactive ion etching) process. After an optical filter 47 is formed in this opening portion by the application with spin coating, resist is peeled off, whereby the optical detecting portion is produced. The wavelength selection characteristic of the optical filter is selected in accordance with the luminescent wavelength or fluorescent wavelength for an object to be measured.

The Cr layer may be used as a light shielding portion on the back face. The Cr layer can be also used as a gate electrode to detect the optimal current value as a field-effect type sensor. While α-Si light receiving element is exemplified in this embodiment, other elements such as pn photodiode, pin photodiode, Schottky photodiode or CCD may be used.

Process 4

As shown in FIG. 3, three substrates of the first substrate 1 which is the silicone substrate, the second substrate 2 which is the glass substrate, and the third substrate 3 provided with a hole for the injection port are bonded together. At this time, an insoluble carrier 6 having a reagent fixed on the surface thereof is enclosed into the accumulation portion 4. The method of bonding substrates is exemplified by pasting with an adhesive or anodic bonding. For example, the anodic bonding with a $CO_2$ laser is possible at lower bonding temperature, whereby adverse effects of the heat on the substrate can be suppressed.

Next, a reagent for use in this embodiment will be described below. The reagent is fixed to the surface of the insoluble carrier enclosed into the accumulation portion, or directly fixed to an inner wall surface of the accumulation portion. The reagent for use in this embodiment contains at least a biological material. The selection of the biological material depends on a material to be analyzed or a sample. That is, the biological material is selected from ones indicating a biological specificity to the sample, thereby making it possible to perform the specific detection.

The biological material referred to herein includes peptide, protein, enzyme, saccharides, lectin, virus, bacteria, nucleic acid such as DNA or RNA, and antibody, natural or synthetic. Particularly effective material in clinical sense among them is exemplified in the following materials: plasma protein such as immunoglobulin, e.g., IgG or IgE, complement, CRP, ferritin, $α_1$ or $β_2$ microglobulin, and an antibody thereof, tumor marker such as α-fetoprotein, carcinoembryonic antigen (CEA), CA19-9 and CA-125, and an antibody thereof, hormones such as luteinizing hormone, follicle-stimulating hormone (FSH), human chorionic gonadotropin (hCG), estrogen and insulin, and an antibody thereof, virus infection relevant substance such as viral hepatitis (relevant) antigen, HIV, ATL and an antibody thereof, bacteria such as diphtheria bacillus, botulinus bacillus, mycoplasma or Treponema pallidum, and an antibody thereof, Protozoas such as Toxoplasma, Trichomonas, Leishmania, Trypanosoma or Malaria, and an antibody thereof, drugs such as antiepileptics, e.g., phenytoin or phenobarbital, antiarrhythmic-drugs such as quinidine, cardiovascular agents such as digoxin, vasodilators such as theophylline, antibiotics such as chloramphenicol or gentamycin, and an antibody thereof, enzymes, exotorin (e.g., streptolysin O) and an antibody thereof. The material causing the antigen-antibody reaction with a substance to be detected in the sample is appropriately selected depending on the kind of the substance to be detected.

When the nucleic acid hybridization is used instead of the antigen-antibody reaction, a nucleic acid probe having a base sequence complementary to that for a nucleic acid to be examined is used.

Figure 10:
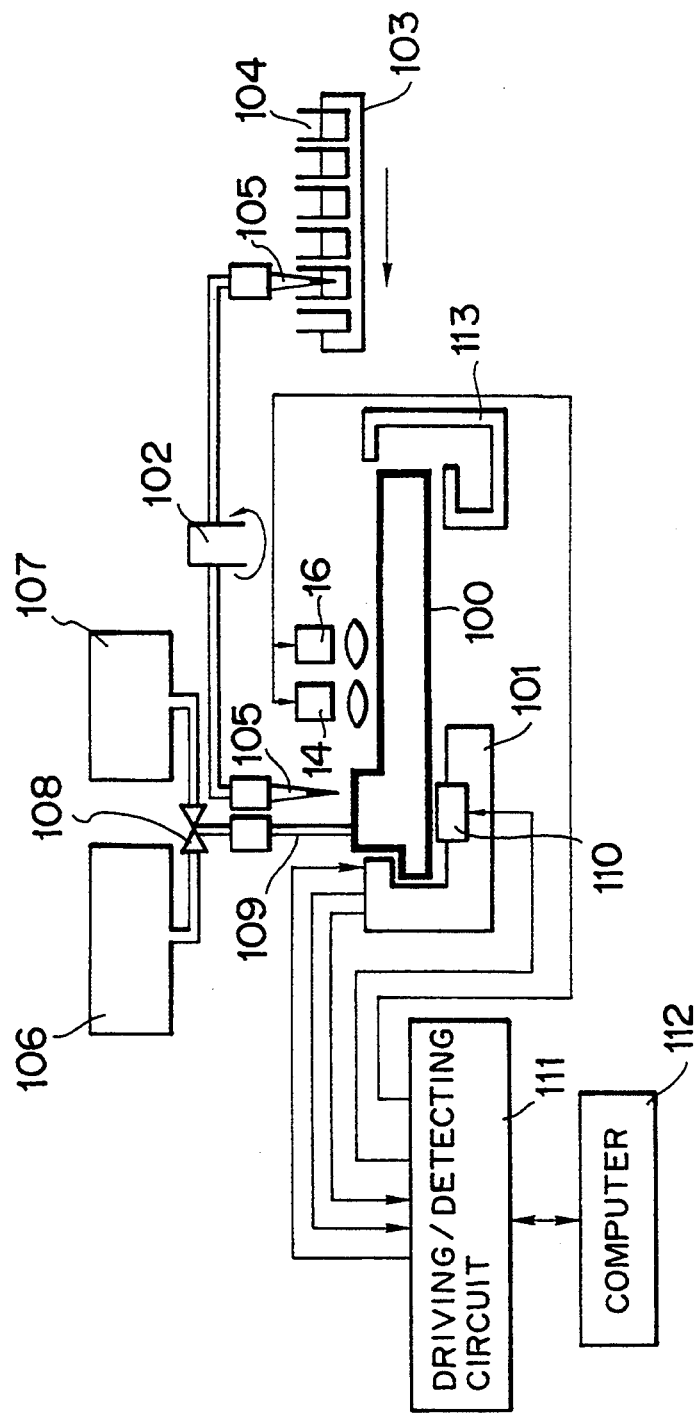
FIG. 10 is a view showing the whole of a measuring system according to an embodiment.

FIG. 10 is a view showing a construction of an entire system for measurement with the above-mentioned cartridge mounted thereon. The cartridge 100 is mounted in a cartridge holder 101. While a single cartridge is only shown in the figure, a plurality of same cartridges may be arranged in parallel, or a cartridge having measuring modules arranged as an array as shown in FIG. 6 may be used to measure a plurality of samples simultaneously or sequentially.

A rack 103 has a plurality of sample vessels 104 arranged therein, in which a plurality of sample liquids are contained. A dispenser apparatus 102 supplies a sample fluid within each sample vessel 104 to the cartridge 100 in sequence, using a pipet 105.

On the other hand, a cleaning liquid vessel 106 contains a cleaning liquid for the B/F separation, while a reagent liquid vessel 107 contains a reaction reagent liquid. A flow passage from each vessel is connected to a valve 108 by which the flow passages are switched to select either of them. A selected liquid is supplied via a tube 109 to the cartridge 100. The pipet 105 and the tube 109 of the dispenser apparatus 102 are both connectable to an injection port of the cartridge 100, so that a desired liquid can be supplied to the cartridge.

An agitator 110 mounted on the cassette holder 101 has the action of agitating the sample fluid and the reagent within the accumulation portion of the cartridge 100 mounted therein, thereby facilitating the reaction. The agitation is performed by moving remotely a magnetic carrier with reagent using a magnet, or vibrating ultrasonically the sample fluid, for example.

In order to improve the accuracy of measured data, it is necessary to control precisely the temperature in the accumulation portion within the cartridge, for this reason the whole of cartridge is held within a thermostatic box (not shown). Also, thermostatic means should be provided for retaining the cleaning liquid, the reaction reagent, and the sample at constant temperatures, as necessary.

An electrode is provided within the cartridge holder 101, and is connected to exposed electrical conductive pattern of the cartridge 100 upon mounting of the cartridge. This electrode is electrically connected to a driving/detecting circuit 111. The circuit 111 performs the driving of light sources 14, 16 for the measurement, the driving of the agitator 110, the driving of the dispenser apparatus 102, the driving of the valve 108, the driving of the micro-pump within the cartridge and the detecting of outputs from two optical detecting elements within the cartridge. A computer 112 performs the control for the entire system and the measurement of the sample based on a detected result. Using the antigen-antibody reaction or nucleic acid hybridization reaction, the coloration reaction, or the fluorescent or scattered light, is detected and data-processed by a well known method such as rate assay or end point. Also, a comparison with prepared analytical curve data is performed. This analytical result is output to a display or printer associated with the computer 112.

Upon measurement by driving the micro-pump, a waste liquid is discharged through the nozzle of the cartridge 100, but the waste liquid is received within a waste liquid vessel 113 and is stored therein. In this embodiment, owing to a heat generating element used as the micro-pump, the waste liquid discharged due to heating or pressure action of bubbles produced is disinfected or sterilized. It is further preferable that the waste liquid is subjected to sterilization action with the waste liquid vessel 113, using means such as heating, ultraviolet ray or drug.

In this way, this system uses a disposable cartridge 100 which is exchanged for each measurement of one sample, thus it can be simplified, resulting in a small-sized, lower cost sample measuring system. Owing to disposability, the micro-pump or sensitive element is not required to have a great durability, and the cartridge can be supplied at lower cost.

In the following, an example of measurement with the above measuring system will be described with steps of detecting a specific DNA in sample.

Step 1

A cartridge is prepared in which a single chain DNA probe for specifically making a hybridization reaction with a specific DNA (single chain) as an object is fixed as an reagent in the accumulation portion. When the cartridge is mounted onto a cartridge holder of the measuring system, the sample fluid containing many DNAs organized to be single chain by pretreatment is injected automatically into the accumulation portion of the cartridge by the pipet of the dispenser apparatus.

Step 2

The sample fluid in the accumulation portion of cartridge is agitated by agitating means provided in the measuring system to facilitate the reaction. If a single chain DNA of the object exists in the sample fluid, hybridization reaction with the DNA probe fixed in the accumulation portion is specifically caused to create a double chain DNA.

Step 3

In order to remove the single chain DNA having not undergone the hybridization reaction, B/F separation is performed by injection and discharge of the cleaning liquid.

Step 4

An enzyme labeling probe is injected into the accumulation portion for enzyme-labeling specifically the double chain DNA produced in the hybridization reaction.

Step 5

B/F separation is performed again by the cleaning to clean away the excess enzyme labeling probe.

Step 6

A reagent liquid containing a substrate indicating the coloration reaction or the fluorescence or chemiluminescence by reacting with the enzyme label is injected into the accumulation portion and reacted.

Step 7

A reaction fluid of the step 6 is flowed to the flow passage portion by activating the micro-pump of the cartridge. The light emitted in the coloration reaction or the fluorescence or chemiluminescence is detected by a light receiving element, so that DNA of the object can be determined from the quantity of the detected light. Also, more accurate determination is allowed by measuring the quantity of the detected light over time with the rate assay method.

The sample measuring cartridge and system as above described can provide the following advantages:

(1) Owing to a micro-pump provided at the downstream of the measuring position, it is possible to make measurement without degenerating or damaging the sample fluid, and offer the disinfection or sterilization action by applying a varied pressure or heat to waste liquid after measurement.

(2) A stable fluid system is obtained, and its control responsiveness for the control of fluid is high. Further, there is almost no dead space, resulting in less amount of sample fluid to be used.

(3) The waste liquid is less produced, and has been disinfected or sterilized, which is preferable from the viewpoint of coping with environmental problems such as a biohazard countermeasure.

(4) The batch production is allowed by using a semiconductor producing process, so that it is possible to manufacture stable-quality and inexpensive cartridges in mass production.

(5) Because of the light receiving element integrated, the adjustment for the alignment of the optical system is unnecessary.

(6) A cartridge in which sample measuring functions are collected intensively, can be supplied with low cost, the cartridge is exchanged for each measurement of one sample, and the constitution of the fluid system is simplified, so that the whole of a measuring system is very compact and highly reliable.

Second Embodiment

Figure 11:
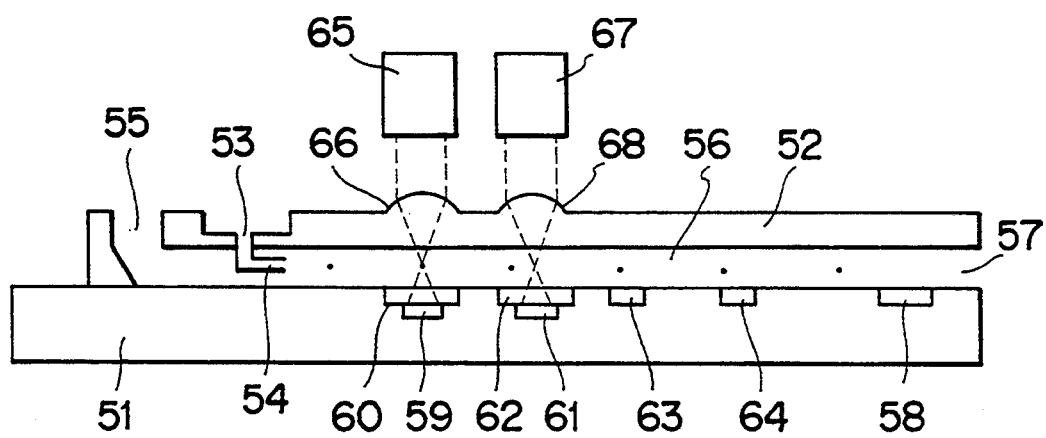
FIG. 11 is a side view showing a constitution of a cartridge according to a second embodiment.
Figure 12:
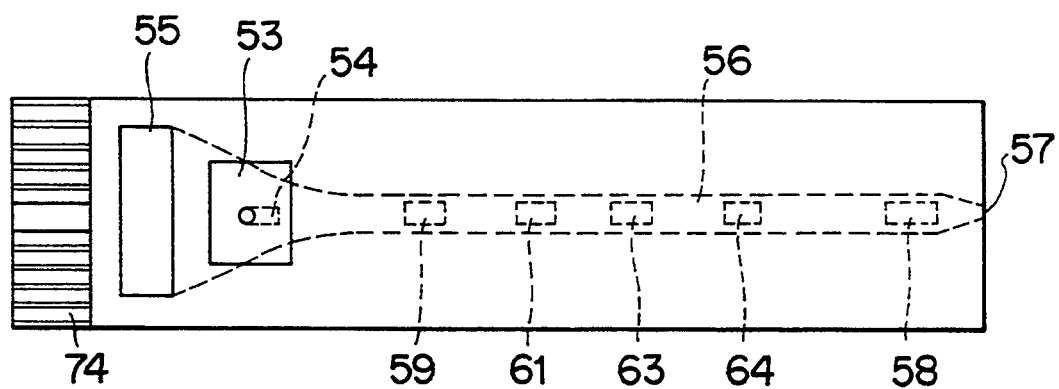
FIG. 12 is a top view in a second embodiment.

Another embodiment of the present invention will be described below by exemplifying a cartridge for the particle measurement in which a sheath flow is created within the flow passage portion by the sample fluid and the sheath fluid, and individual particles in the sample (e.g., blood cells or chromosomes) are sequentially measured. FIG. 11 is a side view showing the structure of the cartridge and FIG. 12 is a top view from above thereof.

The cartridge of this embodiment is also produced by the micromechanics technology including a semiconductor manufacturing process, like in the previous embodiment. The cartridge has a first substrate 51 and a second substrate 52 bonded together, the first substrate 51 being a silicone substrate and the second substrate 52 being a glass substrate. On the upper face of the second substrate 52 is formed a sample receiving portion 53 for receiving the sample fluid containing suspended particles to be measured. A sample tube 54 is connected to the portion 53. A top end of the sample tube 54 projects into the flow passage portion 56. Also, a sheath fluid supply port 55 for supplying a sheath fluid such as isotonic sodium chloride fluid or distilled water is provided and connected to the flow passage portion 56. A nozzle opening 57 is provided, in an outlet port at the top end of the flow passage portion 56. The nozzle opening 57 provides a line resistance action due to its tapered shape. A micro-pump 58 on the first substrate 51 is formed near the nozzle opening 57. The micro-pump 58 has the constitution of attaching a heat generating element (or piezoelectric element) to the flow passage portion by the same manufacturing method as in the previous embodiment, and provides a feed action for the sample fluid by repeating the discharge continuously at a high frequency. Further, the disinfection or sterilization action for the sample fluid which has been already measured, can be provided owing to heating and pressure of the sample fluid generated by the heat generating element of the micro-pump, which is preferable from the viewpoint of biohazard countermeasure.

With this liquid feed action, a fluid flow is formed in the flow passage portion 56, wherein the sample fluid is surrounded in the sheath in accordance with the sheath flow principle to become a slender flow, so that particles in the sample fluid are passed sequentially one by one within the flow passage portion.

On the surface of the first substrate 51, there are provided the micro-pump 58 and a sensitive element for measuring particles in the sample fluid. Specifically, in order to measure the particle optically, a first photodetector element 59, a first optical filter 60 having the wavelength selection characteristic, a second photodetector element 61, and a second optical filter 62 are formed thereon by the same manufacturing method as in the above embodiment, whereby the fluorescent or scattered light emitted from the particle can be detected. It is preferable that the photodetector element is provided with an optical stopper for shielding the direct light incident from a light source. Further, to measure particles electrically, two electrodes 63, 64 are formed on the substrate so as to measure the electrical impedance therebetween. The measured value of electrical impedance is mainly involved in the volume information of particle. The above-mentioned members constitute a measuring portion for measurement of particles in the sample fluid. In this embodiment the measurement of particles is performed either optically or electrically, but is not limited thereto, and may be performed magnetically, for example.

As shown in FIG. 12, a heat generating element 58 for the micro-pump, first and second photodetector elements 59, 61, and electrodes 63, 64 are bonded on the first substrate 51, and are connected with each electrical conductive pattern, like in the previous embodiment. End portions 74 of the conductive patterns are exposed outward so as to contact and electrically conduct with external terminals.

The above-mentioned members are integrally assembled to make up a cartridge. On the other hand, in order to direct the illuminating light which is a measuring energy to a particle flowing within the flow passage portion, light sources 65, 67 are provided apart from the cartridge, as shown in FIG. 11. The light sources 14, 16 emit the light having a wavelength suitable for fluorescence excitation, and suitably a semiconductor laser, for example, can be used therefor. Lens portions 66, 68 for converging the light flux from the light source are formed integrally on an upper face of the second substrate. The light illuminating portion is not limited to this form, but various variations can be conceived as in the previous embodiment. The array formation of measuring module can be also easily made as shown in FIG. 6.

Figure 13:
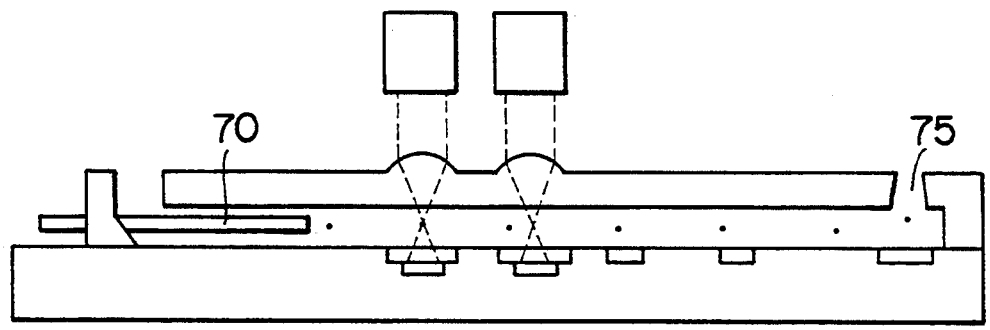
FIG. 13 is a side view of a variation of the second embodiment.
Figure 14:
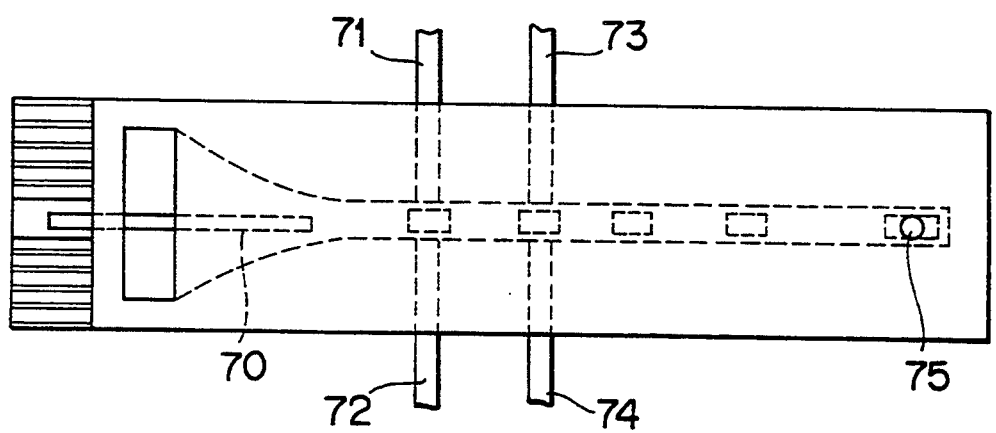
FIG. 14 is a top view of a variation of the second embodiment.

FIGS. 13 and 14 are a side view and a top view of a variation of the cartridge, respectively. In this embodiment, the sheath fluid as well as the sample fluid are supplied from outside, in which one end portion of a sample tube 70 is exposed outward of the cartridge, and connected to a sample supply mechanism externally provided. On both sides of two optical detecting portions, there are embedded optical fibers 70, 71, 72, 73 for receiving the light such as fluorescent or scattered light diverging sideway by the light illumination to a particle, which are led to detector elements (not shown) such as photomultiplier. A nozzle opening 57 is formed as a hole on the upper face of the substrate so as to discharge liquid droplets upward. Other constitutions are the same as in the above embodiment.

Figure 15:
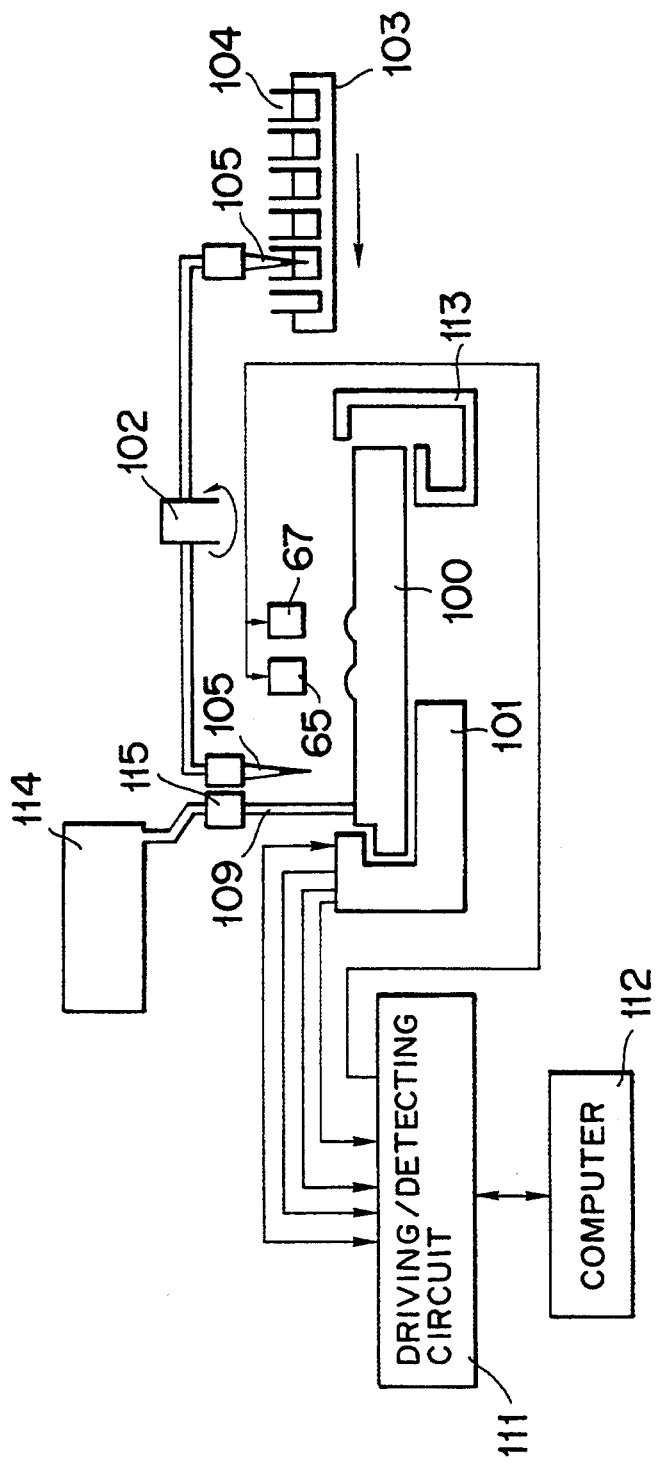
FIG. 15 is a view showing the whole of a measuring system according to the second embodiment.

FIG. 15 is a view showing a construction of an entire system for measurement with the cartridge mounted thereon. The cartridge 100 as previously described is mounted in a cartridge holder 101. While a single cartridge is only shown in the figure, a plurality of same cartridges may be arranged in parallel or a cartridge arranged as an array as shown in FIG. 6 may be used to measure a plurality of samples simultaneously or sequentially.

A rack 103 contains a plurality of sample vessels 104 arranged therein, in which a plurality of sample fluids subjected to pretreatment (e.g., purification treatment or reaction with a reagent) are contained. A dispenser apparatus 102 supplies a sample fluid within each sample vessel 104 to the cartridge 100 in sequence, using a pipet 105.

On the other hand, a sheath fluid vessel 114 containing a sheath fluid such as PH buffer fluid/isotonic sodium chloride fluid or distilled water has a tube 109 connected via a regulator 115 for controlling the flow. A top end portion of the tube 109 is connected to a sheath fluid supply port of the cartridge 100 mounted on a holder 101. The regulator 115 is adjusted to control the sheath flow state.

The cartridge holder 101 is provided with an electrode, which is connected to an exposed electrical conductive pattern of the cartridge 100 upon mounting the cartridge. This electrode is electrically connected to a driving/detecting circuit 111, which performs the driving of light sources 65, 67, the driving of the dispenser apparatus 102, the driving of the regulator 115, the driving of the micro-pump within the cartridge, the detection of outputs from two optical detecting elements within the cartridge, and the detection of electrical impedance between two electrodes. A computer 112 performs the control for the entire system and the analysis of particles based on a detected result. A number of detected data can be obtained from the measurements of individual particles. Various analytical methods for particles using the data are well known including a statistical method such as histogram or cytogram. This analytical result is output to a display or printer associated with the computer 112.

Upon measurement by driving the micro-pump, a waste liquid is discharged through the nozzle of the cartridge 100, but is received within a waste liquid vessel 113 and is stored therein. In this embodiment, owing to a heat generating element used as the micro-pump, the waste liquid discharged due to heating or pressure action of a bubble produced is disinfected or sterilized. It is further preferable that the waste liquid is subjected to sterilization action using means such as heating, ultraviolet ray or drug in the waste liquid vessel 113.

In this way, this system uses a disposable cartridge 100 which is exchanged for each measurement of one sample, thus it can be simplified, resulting in a small-sized, lower cost sample measuring system. Owing to disposability, the micro-pump or sensitive element is not required to have a great durability, and the cartridge can be supplied at a lower cost.

Third Embodiment

Figure 16:
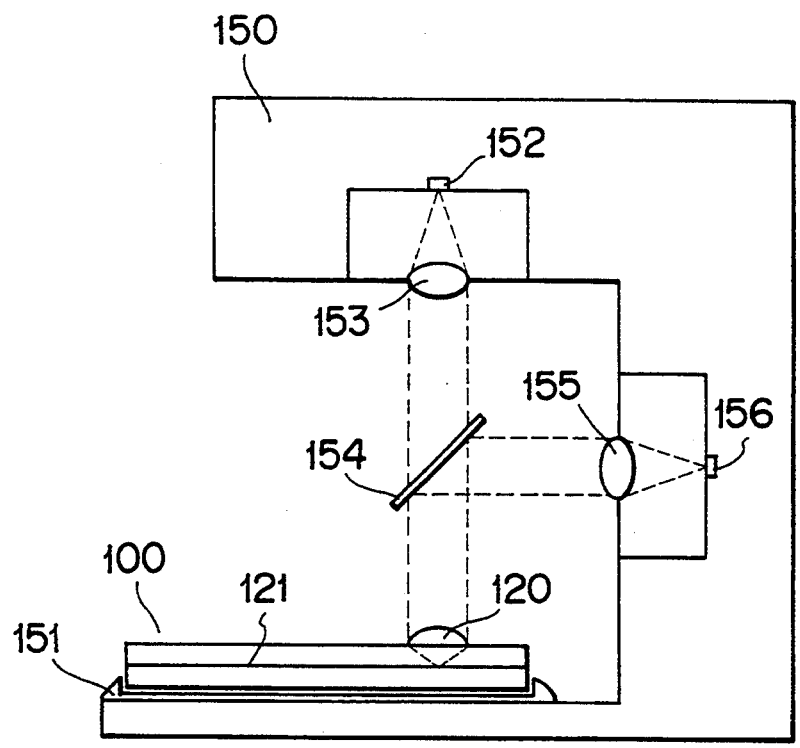
FIG. 16 is a view showing a constitution of a measuring system according to a third embodiment.

FIG. 16 shows a construction of a measuring system according to a further embodiment. In the figure, a reference numeral 150 is a frame, and 151 is a holder. A cartridge 100 is mounted in the holder 151, and is exchanged for each measurement of one sample. The cartridge 100 has substantially the same structure as previously described, with the exception that a condenser lens 120 is formed on the upper face thereof. The condenser lens 120 may be a spherical lens, a Fresnel lens, or a zone plate. A reference numeral 152 is a light source such as a semiconductor laser or a lamp, 153 is a lens for converting the light from the light source 152 into parallel light flux, 154 is a half mirror, 155 is a condenser lens, and 156 is a light receiving element.

In this construction, the light emitted from the light source 152 is converted into parallel light by the lens 153. This light transmits through the half mirror 154 to reach the condenser lens 120 of the cartridge 100. The parallel light is condensed onto a flow path 121 by the condenser lens 120. The condensed light illuminates a sample in the flow path. Herein, among the scattered or fluorescent light radiating in all directions from the sample by the illumination, a component condensed again by the condenser lens 120 into parallel light and reflected at the half mirror 154 is condensed by a lens 155, and is photoelectrically converted by a light receiving element 156 to obtain measured data. Before the light receiving element 156, a wavelength filter (not shown) is disposed to extract only the fluorescent or scattered light component of the object. Instead of the half mirror 154, a dichroic mirror having a characteristic of transmitting the illuminating light wavelength and reflecting the intended fluorescent wavelength may be replaced.

The features of this embodiment will be described below. In the practical use of the system of this embodiment, the mechanical precision in the mounting position for mounting a cartridge to the holder 151 typically falls within a range from about several tens $\mu m$ to several hundreds $\mu m$ in a horizontal direction. Then, there is a possibility of yielding a relative misalignment between an optical axis of the light flux emitted from the light source 152 and a central axis of flow path 121 for the cartridge mounted on the holder by an amount corresponding to a mechanical precision as above mentioned. At this time, if the illuminating light is not parallel, the condensed position of illuminating light may change in accordance with a relative misalignment location between the cartridge and the illuminating light, as shown in FIG. 17B. Assuming the width of the flow path 121 for the cartridge to be 10 $\mu m$, for example, the condensed position may possibly be located out of the flow path 121 in some cases, so that the change in condensed position will exert a great influence on the measurement precision.

On the contrary, this embodiment is characterized in that the light incident upon the cartridge is a parallel light, so that this light is condensed to a central position of the flow path 121 by the condenser lens 120. Thus, the illuminating light is always condensed to a fixed position of the flow path 121, as shown in FIG. 17A, without influence of the precision in the mounting position of the cartridge.

Figure 18:
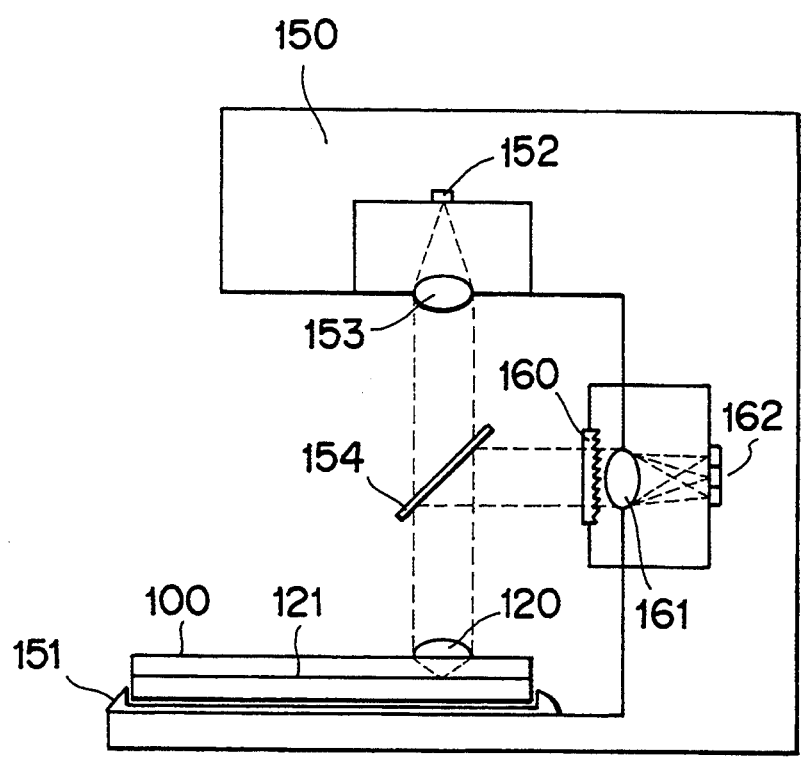
FIG. 18 is a view showing a constitution of a variation of the system as shown in FIG. 16.

FIG. 18 shows a construction of a measuring system which is a variation of FIG. 16. This is similar to the system of FIG. 16, except for the provision of a light receiving system in which more detailed measuring data can be obtained. Same reference numerals in FIG. 18 indicate the same members as in FIG. 16, and the explanation for the same members is omitted. In FIG. 18, a reference numeral 160 is a spectroscopic element such as a grating or prism, 161 is a lens, and 162 is an array-type light receiving element for receiving individually wavelength components of the light separated into spectra. When light is condensed to a sample of the cartridge, like in the previous embodiment, the fluorescent or scattered light is emitted from the sample. Among components of such light, a component condensed again by the condenser lens 120 into parallel light and reflected from the half mirror 154 is separated into spectra by a spectroscopic element 160, which are individually detected via a lens 161 by the light receiving element 162 for each wavelength component. Based on the data thus obtained, more detailed analysis is allowed.

Figure 19:
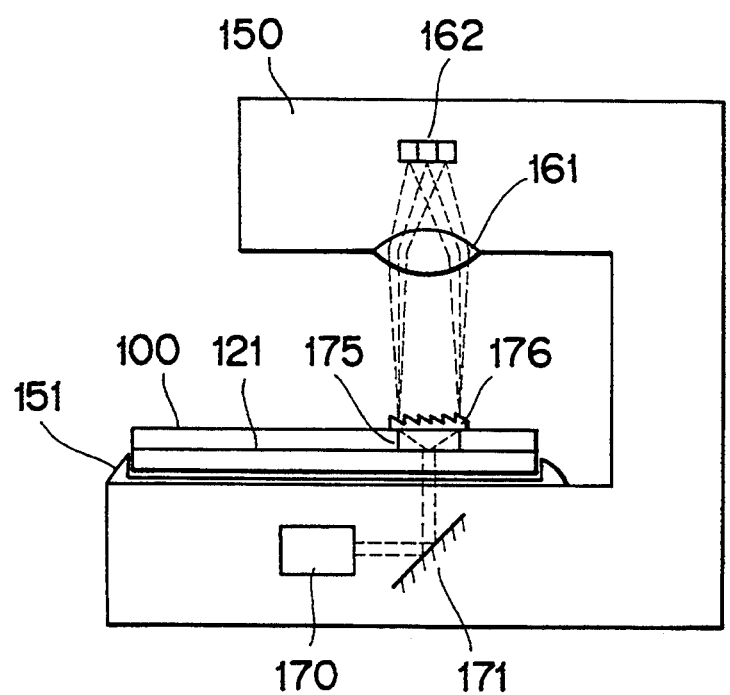
FIG. 19 is a view showing a system constitution of a further variation.
Figure 20:
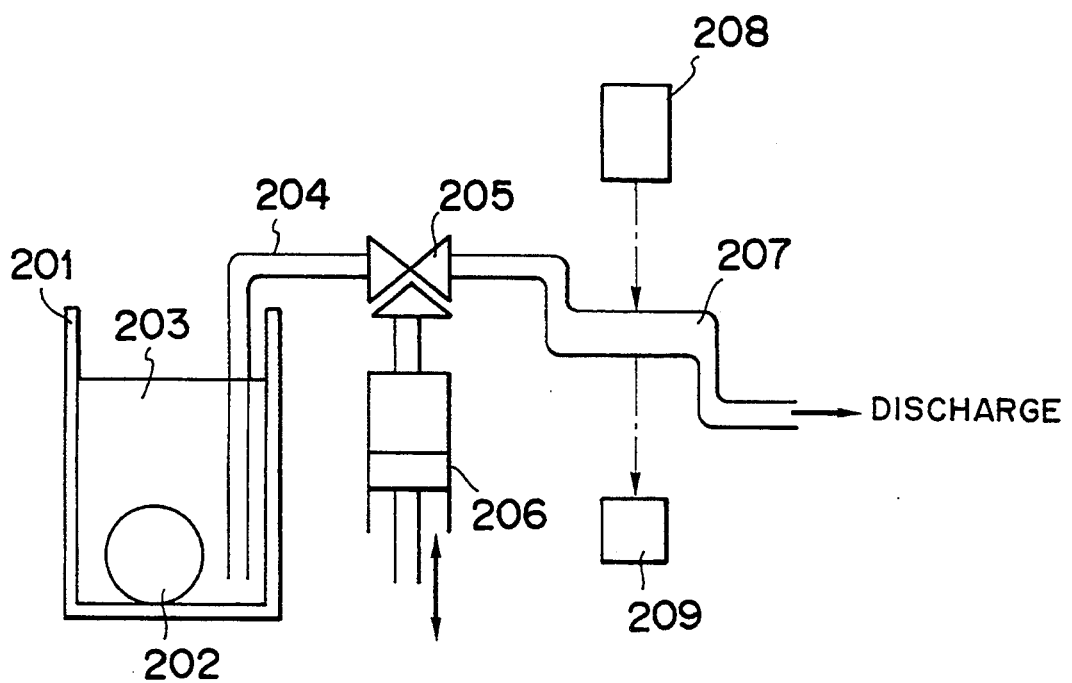
FIG. 20 is a constitutional view of a conventional apparatus.
Figure 21:
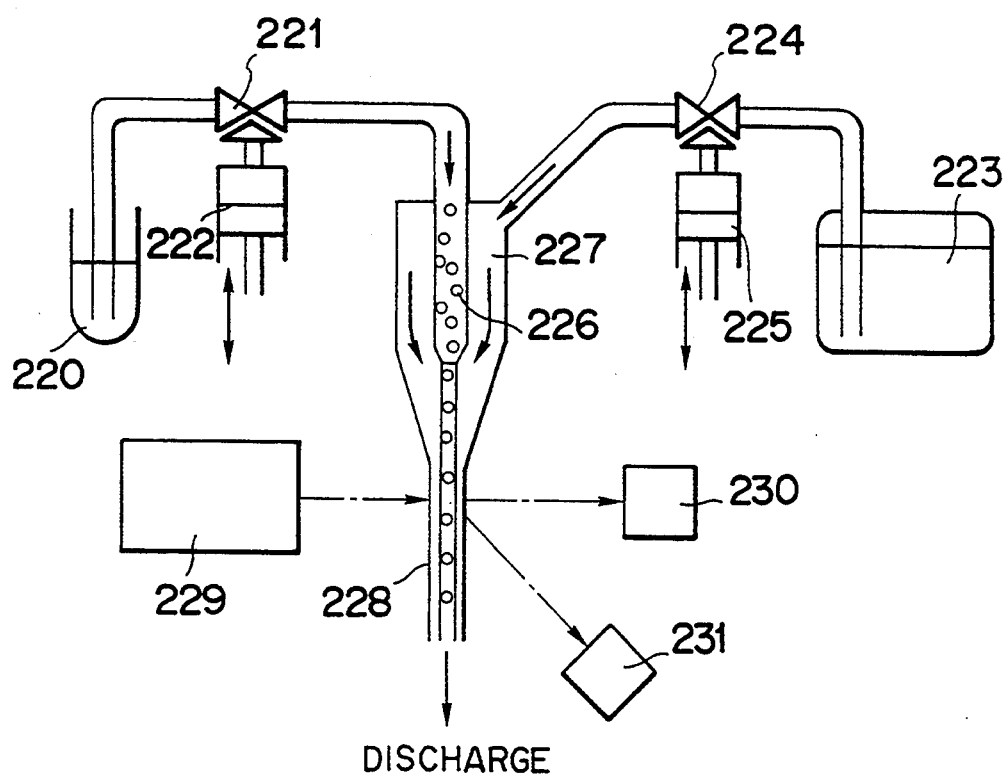
FIG. 21 is a constitutional view of another conventional apparatus.

FIG. 19 is a view showing a construction of a measuring system which is a variation of FIG. 18. This embodiment is characterized in that the cartridge itself has a condensing feature and a spectroscopic feature. In FIG. 19, a reference numeral 170 is a light source for emitting the illuminating light, including a light emitting element and lenses. 171 is a reflecting mirror for directing the illuminating light from the light source 170 toward a measuring position of the cartridge 100 mounted in the holder 151. An illumination system composed of the light source 170 and the mirror 171 is accommodated beneath the frame 150. A light receiving system 162 composed of the lens 161 and the array-type light receiving element 162 is provided above the frame 150. On the other hand, the cartridge 100 is provided with a refractive index distribution type lens 175 and a spectroscopic element 176 such as a grating or prism thereon. A pair of the lens 175 and the spectroscopic element 176 may be replaced with a zone plate having both the condensing feature and the spectroscopic feature.

In this construction, light is directed to a sample of the cartridge mounted from beneath thereof. The fluorescent light emitted therefrom is condensed by the refractive index distribution type lens 175 into parallel light, and is separated into spectra by the spectroscopic element 176. This light is received for each wavelength component by the array-type light receiving element 162 provided at upward of the cartridge 100.

What is claimed is:

1. A sample measuring device comprising:
   an injection port for injecting a sample liquid;
   a flow passage through which said injected sample liquid flows, said flow passage including a measuring portion; and
   a micro-pump including a heat generating element provided downstream of said measuring portion of the flow passage for generating a bubble to feed the sample liquid within said flow passage.

2. A sample measuring device according to claim 1, wherein a sensitive element is provided substantially at said measuring portion.

3. A sample measuring device according to claim 2, wherein a plurality of said sensitive elements are provided along a flowing direction in the flow passage.

4. A sample measuring device according to claim 2, wherein said sensitive element comprises a light receiving element and an optical filter that is provided in front of a light receiving surface of said light receiving element.

5. A sample measuring device according to claim 1, wherein an optical functional element having a light condensing action is formed substantially at said measuring position.

6. A sample measuring device according to claim 5, wherein said optical functional element has an action of condensing parallel light flux incident from outside to the measuring portion in the flow passage.

7. A sample measuring device according to claim 1, further comprising an accumulation portion for accumulating said injected sample liquid, wherein a reagent is enclosed in said accumulation portion.

8. A sample measuring device according to claim 7, wherein said reagent contains a biological material.

9. A sample measuring device according to claim 1, further comprising an introduction port for introducing a sheath fluid along with said sample liquid, wherein a sheath flow is formed in said flow passage.

10. A sample measuring device according to claim 1, which comprises a plurality of said flow passages arrayed in parallel relationship to one another.

11. A sample measuring system comprising:
a holding mechanism for holding a cartridge for measurement of a sample liquid;
measuring means for measuring the sample liquid in said cartridge; wherein said cartridge comprises:
an injection port for injecting a sample liquid;
a flow passage through which said injected sample liquid flows, said flow passage including a measuring portion; and
a micro-pump including a heat generating element provided downstream of said measuring portion of the flow passage for generating a bubble to feed the sample liquid within said flow passage.

12. A sample measuring system according to claim 11, wherein said measuring means includes means for providing a measuring energy to said measuring position.

13. A sample measuring system according to claim 12, wherein said measuring means includes means to measure with optical energy.

14. A sample measuring system according to claim 13, wherein said measuring means comprises a spectroscopic element and a light receiving element.

15. A sample measuring system according to claim 13, wherein a light receiving element for receiving light emitted from said measuring portion is provided inside the cartridge.

16. A sample measuring system according to claim 13, wherein a light receiving element for receiving light emitted from said measuring portion is provided outside the cartridge.

17. A sample measuring system according to claim 13, further comprising means for providing parallel light flux for measurement to said cartridge, wherein said cartridge is provided with an optical functional element for condensing said parallel light to said measuring portion.

* * * * *